United States Patent [19]
Lob

[11] Patent Number: 6,056,750
[45] Date of Patent: May 2, 2000

[54] FIXING ELEMENT FOR OSTEOSYNTHESIS

[76] Inventor: Guenter Lob, Ehrwalder Strasse 82, D-81377 Munich, Germany

[21] Appl. No.: 08/849,279

[22] PCT Filed: Nov. 30, 1995

[86] PCT No.: PCT/DE95/01768

§ 371 Date: Jul. 29, 1997

§ 102(e) Date: Jul. 29, 1997

[87] PCT Pub. No.: WO96/16607

PCT Pub. Date: Jun. 6, 1996

[30] Foreign Application Priority Data

Nov. 30, 1994 [DE] Germany ............... 44 44 510

[51] Int. Cl.$^7$ ................................. A61B 17/58
[52] U.S. Cl. ............... 606/72; 606/77; 606/232
[58] Field of Search ............... 606/72, 73, 76, 606/77, 69, 61, 60, 75, 232, 62, 63, 67, 68

[56] References Cited

U.S. PATENT DOCUMENTS

| | | |
|---|---|---|
| 1,752,752 | 4/1930 | Ogden . |
| 4,484,570 | 11/1984 | Sutter et al. ............... 606/72 |
| 4,696,290 | 9/1987 | Steffee ............... 606/73 |
| 4,716,893 | 1/1988 | Fischer et al. ............... 606/73 |
| 4,760,843 | 8/1988 | Fischer et al. ............... 606/73 |
| 5,209,753 | 5/1993 | Biedermann et al. ............... 606/72 |
| 5,489,210 | 2/1996 | Hanosh ............... 606/72 |
| 5,601,558 | 2/1997 | Torrie et al. ............... 606/72 |
| 5,632,748 | 5/1997 | Beck, Jr. et al. ............... 606/89 |

FOREIGN PATENT DOCUMENTS

| | | |
|---|---|---|
| 0 237 379 | 9/1987 | European Pat. Off. . |
| 0340159 | 11/1989 | European Pat. Off. . |
| 0409364 | 1/1991 | European Pat. Off. . |
| 0 465 408 | 1/1992 | European Pat. Off. . |
| 0 468 600 | 1/1992 | European Pat. Off. . |
| 0464479 | 1/1992 | European Pat. Off. . |
| 0528573 | 2/1993 | European Pat. Off. . |
| 0 551 794 | 7/1993 | European Pat. Off. . |
| 3138311 | 4/1982 | Germany . |
| 1595494 | 9/1990 | U.S.S.R. . |
| 1623633 | 1/1991 | U.S.S.R. . |
| 2014030 | 6/1994 | U.S.S.R. . |

*Primary Examiner*—Michael Buiz
*Assistant Examiner*—David O. Reip
*Attorney, Agent, or Firm*—Venable; Robert Kinberg; Catherine M. Voorhes

[57] ABSTRACT

An osteosynthetical fixing element, for the fixing of a bone implant, includes an accommodating body which is adapted to be introduced into a bone bore-hole and an expanding body, where, as a result of the driving-in of the expanding body into a longitudinally directed opening having a continuous wall, the accommodating body is radially expandable by a wedge effect. The accommodating body is subdivided in the longitudinal direction, and includes at least two sub-elements which form a shaft with a cavity and are separate from one another or are connected to one another so as to be moveable in such a manner that as a result of the driving-in of the expanding body into the cavity, the accommodating body is expandable, substantially over its entire length, as a result of the mutual wedge effect of the accommodating body and expanding body.

13 Claims, 4 Drawing Sheets

FIXING ELEMENT FOR OSTEOSYNTHESIS

BACKGROUND OF THE INVENTION

The invention relates to an osteosynthetical fixing element for the fixing of a bone implant which bone bore-hole and an expanding body which can be driven into an opening of the accommodating body and where the accommodating body is radially expandable by a wedge effect.

EP-B1 409 364 discloses a connecting element for osteosynthesis which is designed as an expandable, elastically deformable sleeve. The sleeve has a diameter which, reduces from an end side and is provided with a slot extending in the longitudinal direction. The expansion of the sleeve is effected by a pin which is designed so as to be axially symmetrical and preferably tapers in conical fashion in the direction of insertion and whose outer diameter is greater than the smallest outer diameter of the sleeve and smaller than the greatest outer diameter thereon. At the periphery of the sleeve different kinds of toothing elements are provided consisting for example of sawtooth-shaped barbs, helical or concentric projections.

Upon the driving-in of the pin, the outer wall of the sleeve, inserted into a corresponding bore in the bone fragments to be connected, is pressed against the surrounding bone material and wedged accordingly.

A disadvantage of the known implant for the osteosynthetic connection of reset bone fragments consists, in particular, in that—independently of the quality of its stabilising effect—primarily the attainable stability of the connection is unpredictable and highly variable in the longitudinal direction.

Furthermore, upon the fixing of this element torsion stresses arise which are unpredictable in terms of their effects and which reduce the stability of the connection.

SUMMARY OF THE INVENTION

Commencing from the shortcomings of the prior art, the object of the invention is to provide a fixing element of the type referred to in the introduction with which an improved osteosynthetic stabilisation, approximating the fixing properties of a metallic fixing element, is attainable.

This object is fulfilled by the instant invention where the accommodating body is subdivided in the longitudinal direction and includes at least two sub-elements which are separate from one another or are connected to one another so as to be movable in such a manner so that the driving-in of the expanding body into the accommodating body results in the accommodating body being expandable, substantially over its entire length, as a result of the mutual wedge effect of the accommodating body and the expanding body.

The invention includes the recognition that, in the case of an osteosynthetic fixing element insertable in an accommodating opening (bore or other longitudinal channel), as uniform as possible an introduction of force should take place for the attainment of a stable connection to the bone. This relates both to the fixing of bone fragments and to the fixing of ligaments to the bone. The corresponding also applies to the fixing of plates. In order to replace the conventionally used screw, an element is required which, solely by virtue of its expansion, facilitates the introduction of force over the entire bone area which is passed through, without the stability of said element being subjected to excess stress. Therefore for example insertion under torsion stress, as in the case of conventional metal screws, is not to be employed.

In contrast to the known conical expanding element, it is provided that the relative expansion takes place over the entire length of the outer surface, which latter is in engagement with the bone material, and by as constant as possible a longitudinal amount sufficient to establish a reliable interlocking connection of the outer profiling. The cross-sectional enlargement relates to that part of the individual sub-elements which is in the leading position during the insertion of the expanding body and thus forms the movement front. Here double triple or also multiple subdivision in the longitudinal direction is possible. Due to the fact that the sub-elements are freely displaceable relative to one another in the radial and tangential directions, in order to be inserted into a bore they are brought into a compressed position in which the wall of the bore has not yet been reached. Instead of bores of circular cross-section, longitudinal channels which have other cross-sectional shapes and/or which are tapered in the direction of insertion are also suitable.

Upon the expansion of the sub-elements (driven through the expanding body which latter bears, as far possible, against the entire length of the inner opening and has uniform, ascending wedge-shaped surfaces), the said sub-elements execute a movement in the radial direction, where a vertical line, which contacts the wall substantially over the entire length, leads in the expansion movement and penetrates into the wall by the full travel distance and over the full length. In the case of two sub-elements, these are two oppositely disposed outer zones, whereas in the case of three sub-elements a structure is formed which resembles the jaws of a drill chuck. Here, however, in contrast to the latter, it is not a question of an engaging action relative to an inner, cylindrical drill but an engagement into the outer wall.

Thus in a preferred embodiment the outer curvature of the sub-elements is to be selected such that it corresponds to the expanded cross-section. Since in this case the lateral lines of the sub-elements initially form a tangent with the bore, it can be favourable to cause the corresponding zone to reduce slightly in cross-section to enable as large as possible a fixing element to be introduced into a given bore-hole and to make the relative expansion movement as large as possible.

In the case of polygonal subdivision, the expanding body is to be of a correspondingly polygonal formation, and a corresponding, similar sliding surface is to be provided for each outer sub-element.

When the fixing element according to the invention is used for the fixing of ligaments or the like in the bore-hole, the peripheral cross-section thereof preferably comprises a corresponding recess for the clamping insertion of the corresponding element.

A peripheral, flange-like collar serves for the fixing of plates and the like.

A particular advantage of the invention consists in that the expansion takes place substantially uniformly over the entire length so that no torsional or rotating movements can arise which could result in non-uniform fixing with the risk of local excess stress.

It is also particularly favorable for the depth of the outer profiling to correspond to the attainable travel so that a compression zone within the structure is available to the displaced bone material.

In accordance with a preferred embodiment, the fixing element for osteosynthesis consists of a substantially rod-shaped accommodating body, comprising two sub-elements which define a cavity, and of an expanding body. The accommodating body, positioned in a bone bore-hole for the connection of bone fragments, changes its spatial configuration when the expanding body enters the cavity, which latter is surrounded by the sub-elements and extends over the entire length of the accommodating body. The sub-elements of the accommodating body are not permanently connected to one another but are retained by guide elements in a relative position to one another such that upon the insertion of the expanding body into the cavity, a uniform change occurs in the spacing between the respective sub-element and the longitudinal axis of the accommodating body in a direction, in each case, at right angles to this axis.

In this way—as previously explained—advantageously it is obtained that the sub-elements are not subjected to deformation as a result of the expansion process and a substantially uniform surface pressure is generated between the outer wall of the fixing element and the bone material over the entire length of the fixing element.

The guide elements are designed as a slide-guide comprising a tongue and a recess which receives the tongue, where the guide elements are in each case disposed on the mutually facing sides of the sub-elements and in active engagement when the fixing element is inserted into a bone bore-hole.

The cavity present between the sub-elements of the accommodating body has a quadrilateral, for example rectangular, cross-section which, in accordance with an advantageous further development of the invention, enlarges in wedge-like formation on one side in an end zone in the direction of the cavity opening. This substantially facilitates the driving-in of an expanding body, having the form of a rod-shaped parallelepiped, during the surgical intervention. The parallelepiped-shaped cross-section is adapted to the rectangular cross-sectional profile of the cavity in the accommodating body, where however the lateral or vertical dimension has a greater value compared to the cross-sectional profile of the cavity in order to obtain the desired expansion effect. Furthermore, for the insertion of the expanding body into the enlarging opening of the accommodating body it is favorable to taper the expanding body by the provision of a wedge-shaped chamfer at the end which is be inserted.

The quadrilateral cross-section of the cavity and of the expanding body, in cooperation with the slide-guide, ensure that, upon the driving-in of the expanding body, a movement of the sub-elements of the accommodating body occurs where the said sub-elements retain their parallelism and their mirror-symmetrical position relative to the axis of the cavity. This facilitates a uniform movement of the sub-elements at right angles to this longitudinal axis and in opposition to one another and brings about a substantially uniform surface pressure between the outer wall of the fixing element and the surrounding bone material over the entire length of the fixing element.

In accordance with another embodiment of the invention, that end of the expanding body which lies opposite the wedge-shaped end portion comprises a profiled wall which forms an enlarged contact surface for the temporary interlocking- and frictional fixing of a surgical tool provided for easy handling of the expanding body. Profile sections of triangular cross-section extending transversely to the longitudinal axis of the expanding body are particularly suitable for this purpose. For the handling of the expanding body it is equally important for the accommodating body to possess a shorter length than the expanding body. This ensures that the profiled end of the expanding body is still able to be handled when the expanding body has already completely penetrated the accommodating body.

In accordance with another favorable further development of the invention, the sub-elements of the accommodating body have the form of longitudinal-section-halves of a hollow cylinder in each case comprising a recess which, upon the assembly of the accommodating body, define a substantially rectangular cavity. On the side on which the expanding body is introduced, the sub-elements in each case bear a flange-like collar which facilitates an accurate and secure positioning of the accommodating body in the bore-hole provided in the bone parts to be connected. In a simple manner, the collar likewise prevents the accommodating body from not being pressed into the bore when the expanding body is being driven in.

The interlocking fixing of the sub-elements of the accommodating body in the bone material is achieved in a favourable manner by a profiled surface of its outer wall. For this purpose grooves are provided which are arranged in the form of a half-ring and which have a triangular cross-section. The number and/or shape of the grooves is selected such that a longitudinal section through the sub-elements has a sawtooth-shaped boundary line.

In accordance with another further development of the invention, the sub-elements have a different cross-sectional profile. Here in the case of one sub-element the periphery thereof is provided with a flattened area extending over the entire length. Advantageously, when an accommodating body is inserted into the bone bore-hole this results in an additional free space between the respective walls, in which free space a further element to be permanently attached to the bone can be positioned. This feature of the invention provides, for example, favorable osteosynthetic conditions for a knee joint operation where, for the fixing of the cruciate ligament, a bone portion with grown-on tendon is inserted in such a free space and can be fixed by the expansion of the accommodating body.

Both the accommodating body and the expanding body consist of a material which, with acceptable biological compatibility, is subject to resorbing decomposition and is produced by injection molding. A polylactide, polyglycolide or clockwise- or anticlockwise-rotatory copolymer of these substances is preferably provided as the material.

BRIEF DESCRIPTION OF THE DRAWINGS

The invention and advantageous further developments thereof and will be explained in detail in the following together with the description of the preferred embodiment of the invention making reference to the Figures wherein.

DESCRIPTION OF THE PREFERRED EMBODIMENT

Figure 1A:
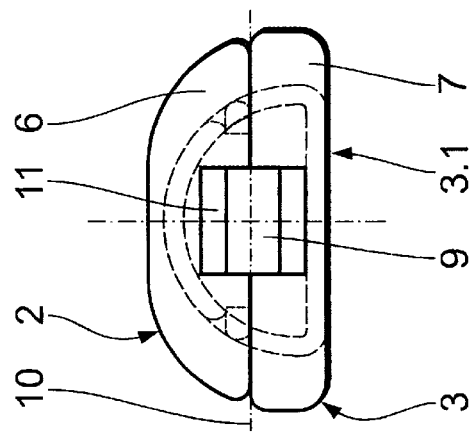
FIG. 1*a* is a lateral view from the right corresponding to the illustration in FIG. 1.
Figure 1:
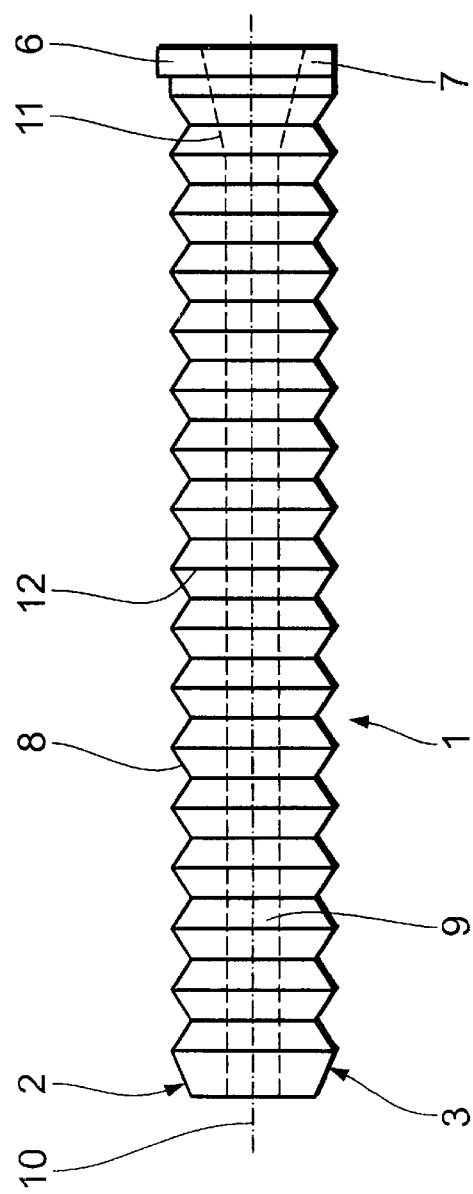
FIG. 1 is a front view of the preferred embodiment of the invention in the unexpanded state.
Figure 2A:
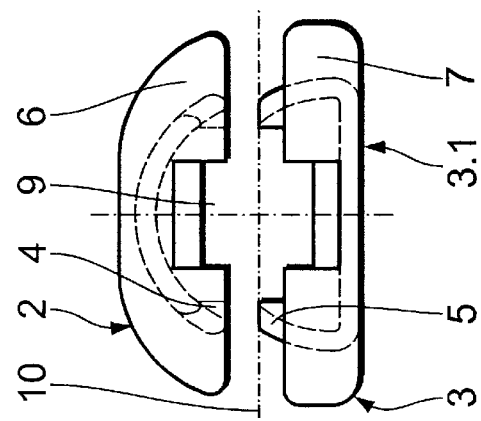
FIG. 2*a* is a lateral view from the right corresponding to the illustration in FIG. 2.
Figure 2:
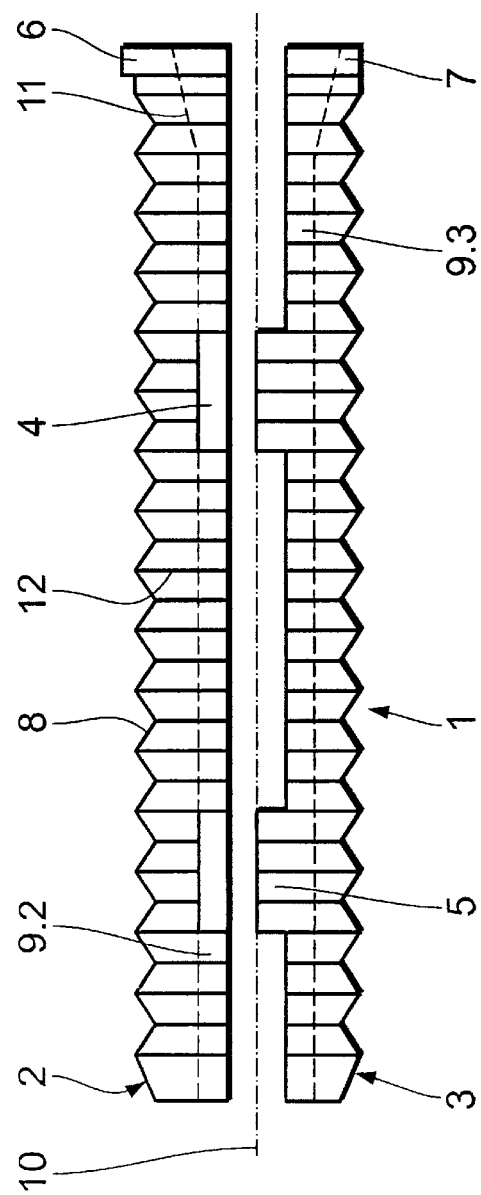
FIG. 2 is a front view of the preferred embodiment of the invention following the driving-in of an expanding body (not shown)

The accommodating body 1, illustrated in a front view and side view in FIGS. 1 and 1*a* respectively, is composed of two rod-shaped sub-elements 2 and 3 of different formation comprising an equal-sized, axially extending, rectangular recess (compare items 9.2 and 9.3 in FIGS. 2 and 2a). The sub-elements 2, 3 are not permanently connected to one another. They are retained in the illustrated position by guide elements (compare items 4 and 5 in FIGS. 2 and 2a) and form a hollow-cylindrical body which is flattened on one side. The recesses in the sub-elements 2, 3 define a cavity 9 of rectangular cross-section which extends over the entire length of the accommodating body 1. One end zone of the cavity 9 is provided with a wedge-shaped enlargement 11 in the direction of the cavity opening. This substantially simplifies the driving-in of an expanding body in the form of an oblong parallelepiped (not shown, compare item, 20 in FIG. 3) during the surgical intervention.

As a result of the one-sided flattening 3.1 at the periphery of the sub-element 3, advantageously a free space is provided between the accommodating body 1 inserted into a bone bore-hole and the wall of said bore-hole, into which free space an additional element, to be osteosynthetically connected, can be introduced prior to the driving-in of the expanding body. This shape of the fixing element thus provides favorable conditions for knee joint operations in which a cruciate-ligament attachment is provided.

Each of the sub-elements 2, 3 bears a flange-like collar 6, 7, in each case at the same end. This collar ensures that an accommodating body 1, introduced into a bone bore-hole during an osteosynthetic intervention, remains in the desired position when the expanding body is inserted into the cavity 9 along the axis 10.

When an accommodating body 1 has been inserted into a bore -hole, the profiling provided at the periphery of the sub-elements 2, 3 results in the fixing of said accommodating body and a favorable introduction of force into the-bone when the expanding body is driven into the cavity 9. The profiling is formed by similar, triangular-shaped grooves 8 which extend around the sub-elements in each case in the form of a half-ring and converge in peripheral edges 12.

The accommodating body 1 shown in FIGS. 2 and 2a is enlarged in its spatial configuration by an expanding body (not shown) driven into the cavity 9. Here the sub-elements 2, 3 have been displaced in opposite directions and in each case by the same amount in a direction at right angles to the cavity axis 10. This movement is brought about by the slide-guide, which latter comprises a tongue 5 and a rectangular recess 4, and by the rectangular shape of the recesses 9.2, 9.3 defining the channel 9 and of the rod-shaped expanding body, and ensures a uniform pressure by the profiled wall of the sub-elements 2, 3 against the bone material over the entire length of the fixing element.

Figure 3:
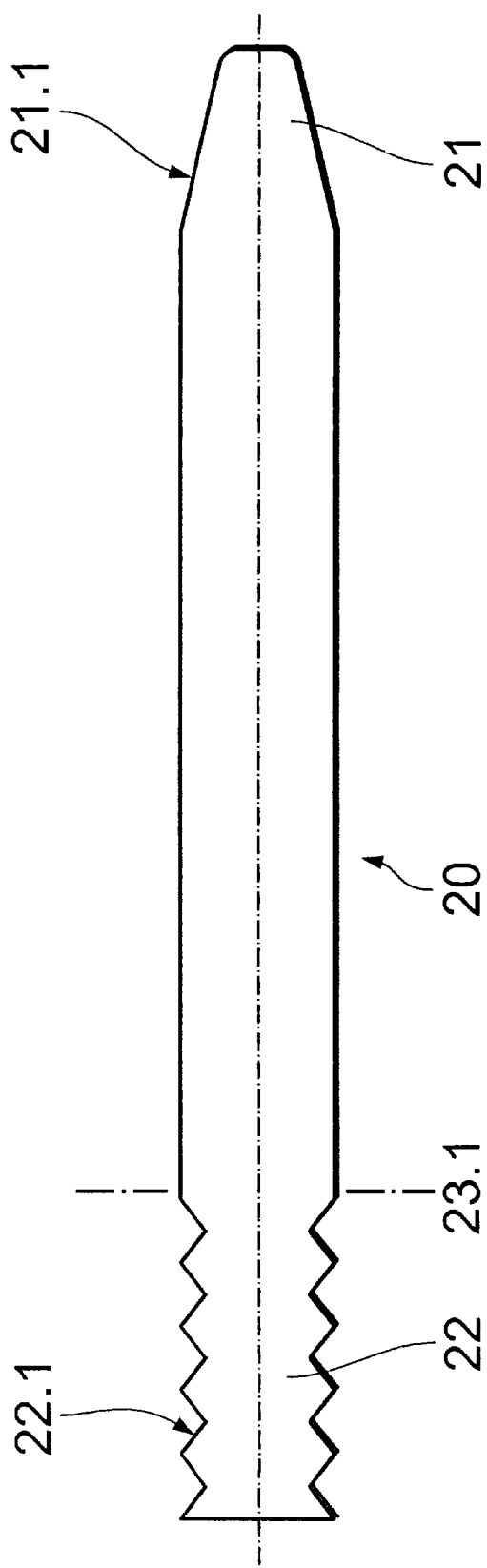
FIG. 3 is a lateral view of a favorable embodiment of an expanding body.

The expanding body 20, illustrated in FIG. 3, of the fixing element consists, like the sub-elements of the accommodating body, of a material which is subject to resorbing decomposition in the human body. The rod-shaped expanding body has a rectangular cross-sectional profile and at one of its ends 21 forms a wedge-shaped chamfer 21.1 which substantially simplifies the insertion of the expanding body into an accommodating body positioned in the bone material. At the other end 22 profiling 22.1 is provided to enable a more secure positioning of a tool for the handling of the expanding body during an osteosynthetic intervention. The profiling consists of ribs of triangular cross-section which extend transversely to the longitudinal axis of the expanding body.

Figure 4:
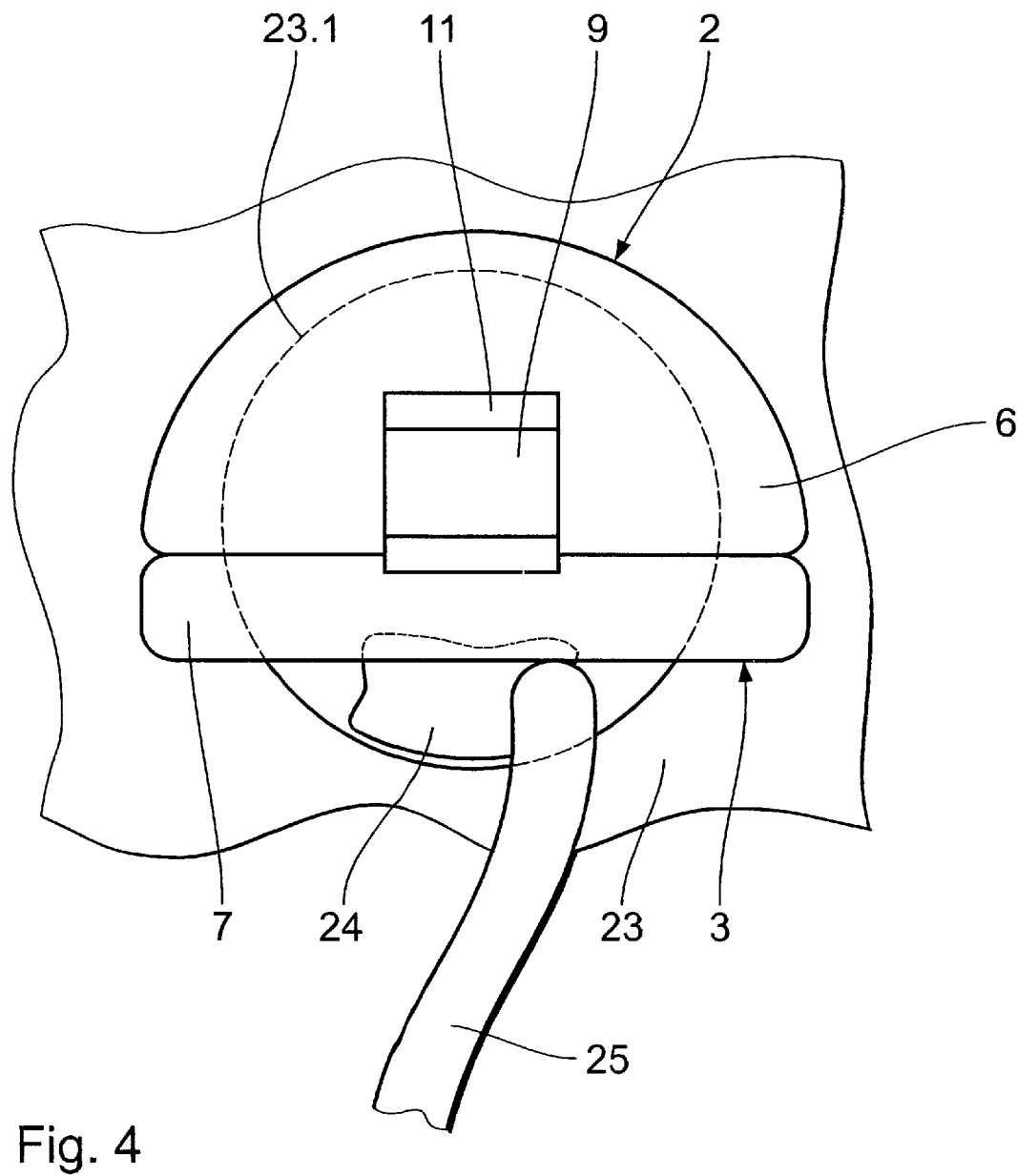
FIG. 4 is a plan view of a bone area with an inserted fixing element in a schematic illustration.

The bone area 23 illustrated in FIG. 4 comprises a bore-hole 23.1 into which the accommodating body, comprising the sub-elements 2 and 3, is inserted. Due to the flattening at the periphery of sub-element 3, a free space remains between the wall of the bore-hole and the accommodating body. This free space can be utilized for the insertion of elements 24, 25 to be attached during an osteosynthetic intervention. Thus for example in the case of a knee joint operation with cruciate-ligament replacement, the free space provides favorable conditions for the positioning of a bone portion with tendon 25 attached thereto. Following the driving-in of the expanding body (not shown), bone portion 24 and tendon 25 elements of the sub-element 3 are pressed against the wall of the bone in a fixing manner.

The invention is not limited to the preferred exemplary embodiment described in the foregoing. Rather, a number of variants are conceivable which also apply the described invention in basically different types of embodiments.

I claim:

1. An osteosynthetical fixing element, for the fixing of a bone implant, comprising an accommodating body made from a bioresorbable material which is adapted to be introduced into a bone bore-hole and an expanding body, where, as a result of the driving-in of the expanding body into a longitudinally directed opening having a continuous wall, the accommodating body is radially expandable by a wedge effect, wherein the accommodating body, sub-divided in the longitudinal direction, comprises at least two sub-elements which form a shaft with a cavity and are separate from one another or are connected to one another so as to be moveable in such a manner that as a result of the driving-in of the expanding body into the cavity, the accommodating body is uniformly radially expandable, substantially over its entire length, as a result of the mutual wedge effect of the accommodating body and expanding body.

2. A fixing element according to claim 1, wherein the cavity formed by the at least two sub-elements is cylindrical on one side and has a substantially polygonal cross-section on the other side.

3. A fixing element according to claim 1, wherein the at least two sub-elements complement one another to form a body having a substantially cylindrical outer wall of uniform cross-section.

4. A fixing element according to claim 3, wherein in the outer peripheral area, at least over a part of their longitudinal extent, the at least two sub-elements comprise profiling or structuring which extends substantially transversely to the direction of insertion of the fixing element into the bone and the profiling consists of grooves of triangular cross-section which engage around the sub-elements substantially in the form of a half-ring.

5. A fixing element according to claim 1, wherein at least two of the sub-elements have different cross-sectional shapes in the shaft area.

6. A fixing element according to claim 5, wherein at least one sub-element comprises an outer flattening of its outer curvature extending over at least a part of the length of the shaft.

7. A fixing element according to claim 1, wherein at least one of the sub-elements is provided with a flange-like collar.

8. A fixing element according to claim 1, further including an engaging element in the form of a tangentially extending tongue, said engagement element being provided on one of the sub-elements or a corresponding engaging element and being designed for engagement into a recess provided in the other sub-element for the guiding accommodation of the tongue.

9. A fixing element according to claim 1, wherein the cavity enlarges slightly in wedge-shaped formation towards that end of the sub-element which bears a flange-like collar.

10. A fixing element according to claim 1, wherein the end of the expanding body which has a smaller cross-section comprises a substantially wedge-shaped chamfer and/or the length of the expanding body exceeds the length of the sub-elements.

11. A fixing element according to claim 10, wherein the end of the expanding body which is at the rear upon insertion comprises profiling to improve the engagement of a tool.

12. A fixing element according to claim 11, wherein the profiling is provided on two side surfaces arranged opposite one another and comprises profile elements, extending transversely to the longitudinal axis of the expanding body, of preferably triangular cross-section.

13. A fixing element according to claim 1, wherein polylactide, polyglycolide or a clockwise- or anticlockwise-rotatory copolymer of these substances is provided as resorbable material.

* * * * *